(12) United States Patent
Overhage et al.

(10) Patent No.: US 12,633,419 B2
(45) Date of Patent: May 19, 2026

(54) SYSTEM AND METHODS FOR GENERATING AND LEVERAGING A DISEASE-AGNOSTIC MODEL TO PREDICT CHRONIC DISEASE ONSET

(71) Applicant: CERNER INNOVATION, INC., Kansas City, KS (US)

(72) Inventors: Joseph Marcus Overhage, Zionsville, IN (US); Cole Anthony Erdmann, Kansas City, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 648 days.

(21) Appl. No.: 16/951,601

(22) Filed: Nov. 18, 2020

(65) Prior Publication Data
US 2021/0183525 A1 Jun. 17, 2021

Related U.S. Application Data

(60) Provisional application No. 62/948,991, filed on Dec. 17, 2019.

(51) Int. Cl.
*G16H 50/70* (2018.01)
*G16H 50/20* (2018.01)

(52) U.S. Cl.
CPC ............. *G16H 50/70* (2018.01); *G16H 50/20* (2018.01)

(58) Field of Classification Search
None
See application file for complete search history.

(56) References Cited

U.S. PATENT DOCUMENTS

| | | | | |
|---|---|---|---|---|
| 10,867,701 B1 * | 12/2020 | Anhold | .................. | G16H 10/40 |
| 2017/0000422 A1 * | 1/2017 | Moturu | ............... | A61B 5/0022 |
| 2017/0308981 A1 * | 10/2017 | Razavian | ............... | G16H 40/60 |

(Continued)

FOREIGN PATENT DOCUMENTS

| | | | | |
|---|---|---|---|---|
| CN | 111145910 A | * | 5/2020 | ............. G06F 18/23 |

OTHER PUBLICATIONS

Razavian, N., Marcus, J., & Sontag, D. (2016). Multi-task prediction of disease onsets from longitudinal lab tests. Ithaca: Cornell University Library, arXiv.org. Retrieved from https://dialog.proquest.com/professional/docview/2080880550?accountid=131444 (Year: 2016).*

(Continued)

*Primary Examiner* — Robert A Sorey
(74) *Attorney, Agent, or Firm* — Invoke

(57) ABSTRACT

Methods, systems, and computer-readable media are disclosed herein for generating a disease-agnostic data model that can be used to predict the onset of multiple chronic diseases in individual patients. In an aspect, the data model is made by autonomously selecting features from longitudinal medical records of patients having chronic diseases that will become predictors for the onset of a chronic disease. The features are vectorized around a disease onset date and processed through a recurrent neural network to produce the data model. Then, the data model may leveraged to predict, for new longitudinal medical records that are input, a future time period when another patient is predicted to experience the onset of the chronic disease. The same data model may utilized to make predictions for multiple chronic diseases.

22 Claims, 8 Drawing Sheets

(56) References Cited

U.S. PATENT DOCUMENTS

| | | | | |
|---|---|---|---|---|
| 2019/0088367 A1* | 3/2019 | Stamatopoulos | ...... | G16H 50/20 |
| 2019/0311790 A1* | 10/2019 | Dadkhahnikoo | ...... | G16H 80/00 |
| 2020/0303074 A1* | 9/2020 | Mueller-Wolf | ...... | A61B 5/7275 |
| 2020/0327404 A1* | 10/2020 | Miotto | ................ | G06F 18/2415 |
| 2020/0411164 A1* | 12/2020 | Donner | ................. | G16H 30/20 |
| 2021/0183525 A1* | 6/2021 | Overhage | ............. | G16H 50/70 |
| 2023/0010686 A1* | 1/2023 | Lesh | ..................... | G16H 50/70 |

OTHER PUBLICATIONS

Kale, D. C. (2018). Learning to diagnose from electronic health records data (Order No. 27794973). Available from ProQuest Dissertations and Theses Professional. (2383539312). Retrieved from https://dialog.proquest.com/professional/docview/2383539312?accountid=131444 (Year: 2018).*

Edward Choi, Mohammad Taha Bahadori, Andy Schuetz, Walter F. Stewart, Jimeng Sun Proceedings of the 1st Machine Learning for Healthcare Conference, PMLR 56:301-318, 2016. (Year: 2016).*

\* cited by examiner

100

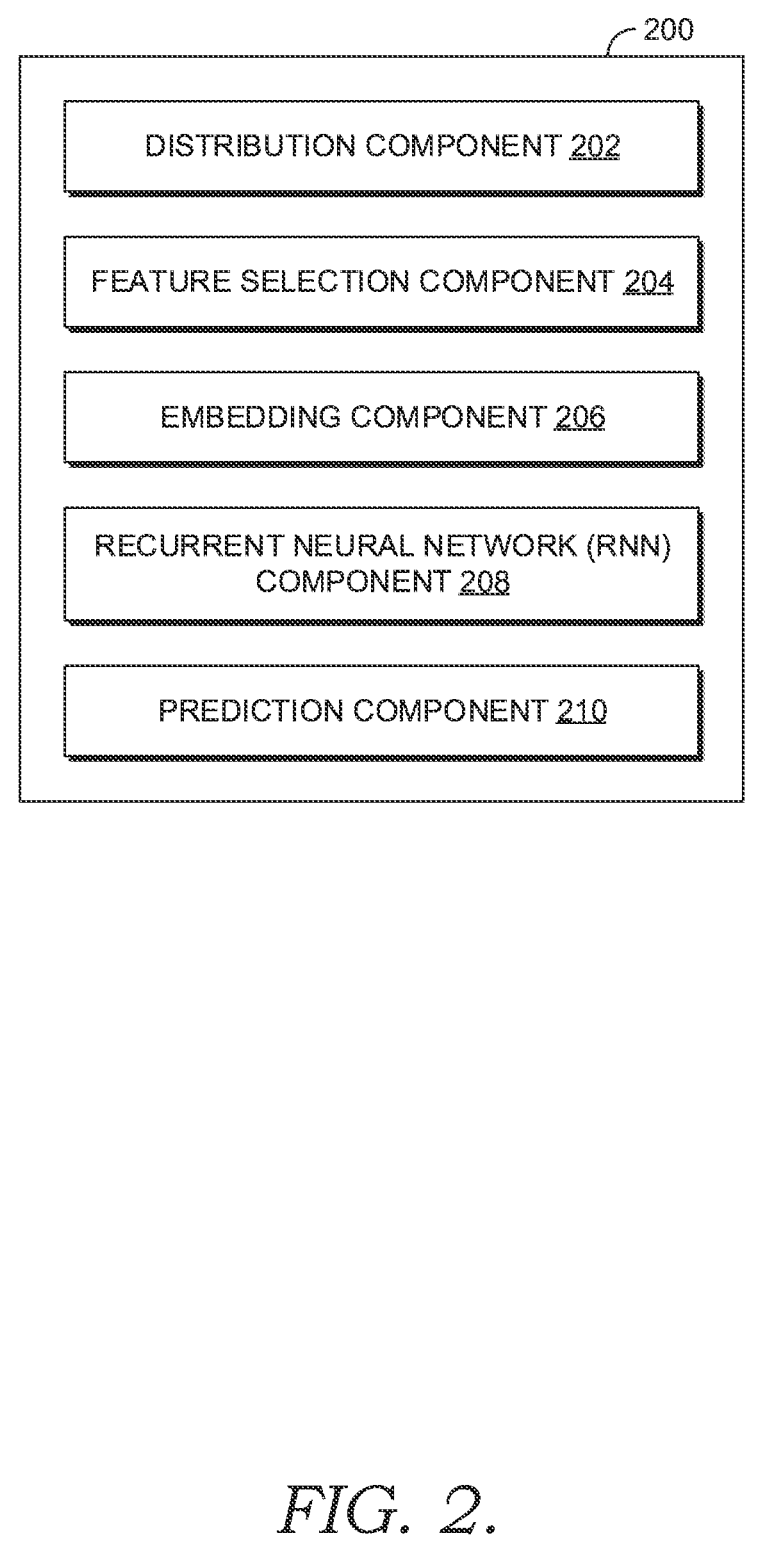

200

DISTRIBUTION COMPONENT 202

FEATURE SELECTION COMPONENT 204

EMBEDDING COMPONENT 206

RECURRENT NEURAL NETWORK (RNN) COMPONENT 208

PREDICTION COMPONENT 210

*FIG. 2.*

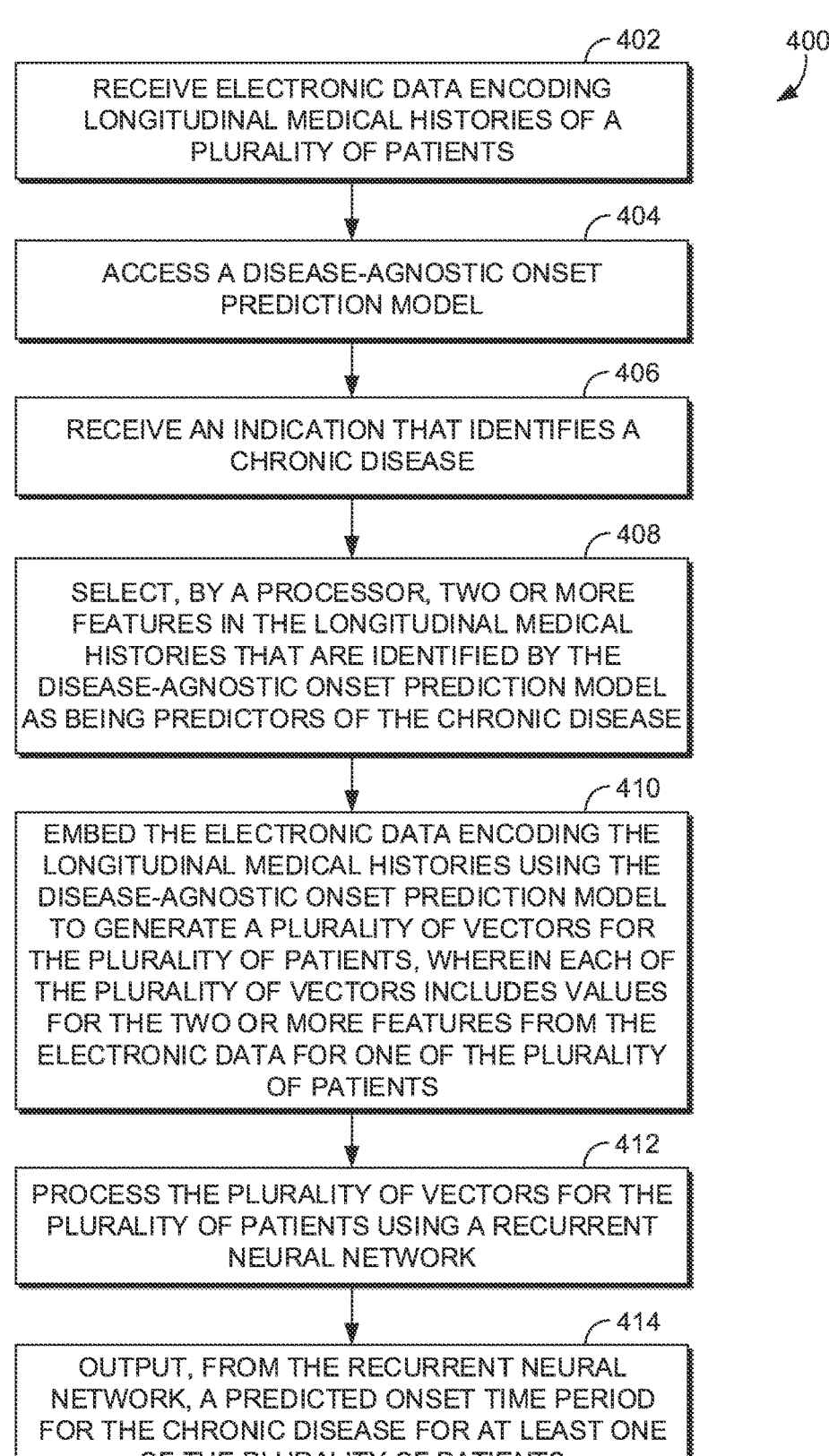

402

400

RECEIVE ELECTRONIC DATA ENCODING LONGITUDINAL MEDICAL HISTORIES OF A PLURALITY OF PATIENTS

404

ACCESS A DISEASE-AGNOSTIC ONSET PREDICTION MODEL

406

RECEIVE AN INDICATION THAT IDENTIFIES A CHRONIC DISEASE

408

SELECT, BY A PROCESSOR, TWO OR MORE FEATURES IN THE LONGITUDINAL MEDICAL HISTORIES THAT ARE IDENTIFIED BY THE DISEASE-AGNOSTIC ONSET PREDICTION MODEL AS BEING PREDICTORS OF THE CHRONIC DISEASE

410

EMBED THE ELECTRONIC DATA ENCODING THE LONGITUDINAL MEDICAL HISTORIES USING THE DISEASE-AGNOSTIC ONSET PREDICTION MODEL TO GENERATE A PLURALITY OF VECTORS FOR THE PLURALITY OF PATIENTS, WHEREIN EACH OF THE PLURALITY OF VECTORS INCLUDES VALUES FOR THE TWO OR MORE FEATURES FROM THE ELECTRONIC DATA FOR ONE OF THE PLURALITY OF PATIENTS

412

PROCESS THE PLURALITY OF VECTORS FOR THE PLURALITY OF PATIENTS USING A RECURRENT NEURAL NETWORK

414

OUTPUT, FROM THE RECURRENT NEURAL NETWORK, A PREDICTED ONSET TIME PERIOD FOR THE CHRONIC DISEASE FOR AT LEAST ONE OF THE PLURALITY OF PATIENTS

*FIG. 4.*

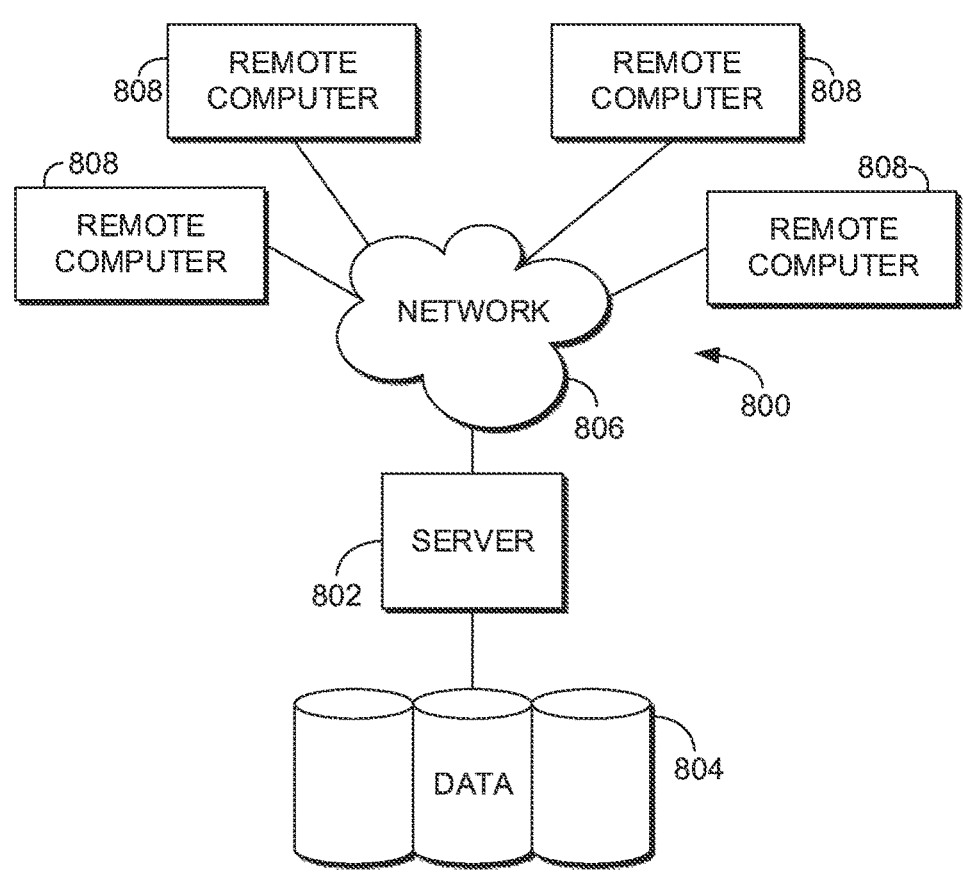
*FIG. 8.*

SYSTEM AND METHODS FOR GENERATING AND LEVERAGING A DISEASE-AGNOSTIC MODEL TO PREDICT CHRONIC DISEASE ONSET

CROSS REFERENCE TO RELATED APPLICATION

This patent application is a non-provisional application that claims the benefit of and priority to U.S. Provisional App. No. 62/948,991, filed on Dec. 17, 2019, the entirety of which is incorporated herein by reference.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

One aspect of the present disclosure relates to a non-transitory computer-readable storage medium having instructions embodied thereon, the instructions being executable by one or more processors to perform a method for automated generation of a disease-agnostic onset prediction model. In the method, electronic data encoding longitudinal medical histories of a plurality of patients and an indication of a chronic disease are received. A plurality of distributions for a plurality of features in the longitudinal medical histories of a plurality of patients encoded in the electronic data are automatically generated, in an aspect. Via one or more processors, two or more of the plurality of features are automatically selected from the distributions, wherein the two or more of the plurality of features are selected as corresponding to the chronic disease, in some aspects. A first plurality of vectors for the plurality of patients are embedded, wherein the first plurality of vectors includes the two or more of the plurality of features selected as corresponding to the chronic disease. Also, a second plurality of vectors for a plurality of medical concepts identified in the electronic data encoding longitudinal medical histories of a plurality of patients is embedded. The first and second plurality of vectors are processed using a recurrent neural network, in various aspects, wherein processing includes aligning sequential observation time periods of the longitudinal medical histories relative to known dates of onset of the chronic disease for two or more of the plurality to patients. The recurrent neural network outputs a disease-agnostic onset prediction model based on the first and second plurality of vectors as processed, in an aspect.

In another aspect, the present disclosure relates to a non-transitory computer-readable storage medium having instructions embodied thereon, the instructions being executable by one or more processors to perform a method for automatically predicting patient onset of chronic disease based on a disease-agnostic onset prediction model. In aspects, electronic data encoding longitudinal medical histories of a plurality of patients is received. A disease-agnostic onset prediction model is accessed, in some aspects. An indication that identifies a chronic disease is received. Two or more features from the longitudinal medical histories are selected, via a processor, as identified by the disease-agnostic onset prediction model as being predictors of the chronic disease, in some aspects. The electronic data encoding the longitudinal medical histories is embedded, in an aspect, using the disease-agnostic onset prediction model to generate a plurality of vectors for the plurality of patients, wherein each of the plurality of vectors includes values for the two or more features from the electronic data for one of the plurality of patients. The plurality of vectors for the plurality of patients using a recurrent neural network, in some aspects. From the recurrent neural network a predicted onset time period for the chronic disease is output for at least one of the plurality of patients.

In one aspect, the present disclosure relates to a system for a disease-agnostic onset prediction model. In aspects, the system includes a recurrent neural network, a first layer that is an embedding layer, a second layer that is a connected layer, and one or more processors. The one or more processors of the system are configured to receive electronic data encoding longitudinal medical histories of a plurality of patients and access a disease-agnostic onset prediction model. In one aspect, the system receives an indication that identifies a chronic disease. The system selects, via the one or more processors, two or more features from the longitudinal medical histories that are identified by the disease-agnostic onset prediction model as being predictors of the chronic disease, in some aspects. Then, the system embeds the electronic data encoding the longitudinal medical histories using the disease-agnostic onset prediction model to generate a plurality of vectors for the plurality of patients, in aspects, wherein each of the plurality of vectors includes values for the two or more features from the electronic data for one of the plurality of patients. The plurality of vectors for the plurality of patients are processed using a recurrent neural network, in some aspects. Then, a predicted onset time period for the chronic disease for at least one of the plurality of patients is output from the recurrent neural network of the system.

BRIEF DESCRIPTION OF THE DRAWINGS

Illustrative aspects of the present invention are described in detail below with reference to the attached drawing figures, and wherein:

FIG. 2 depicts a computing device, in accordance with aspects;

FIG. 4 depicts a method for automatically predicting patient onset of chronic disease based on a disease-agnostic onset prediction model, in accordance with aspects;

FIG. 8 depicts a computing environment, in accordance with aspects.

DETAILED DESCRIPTION

Figure 1:
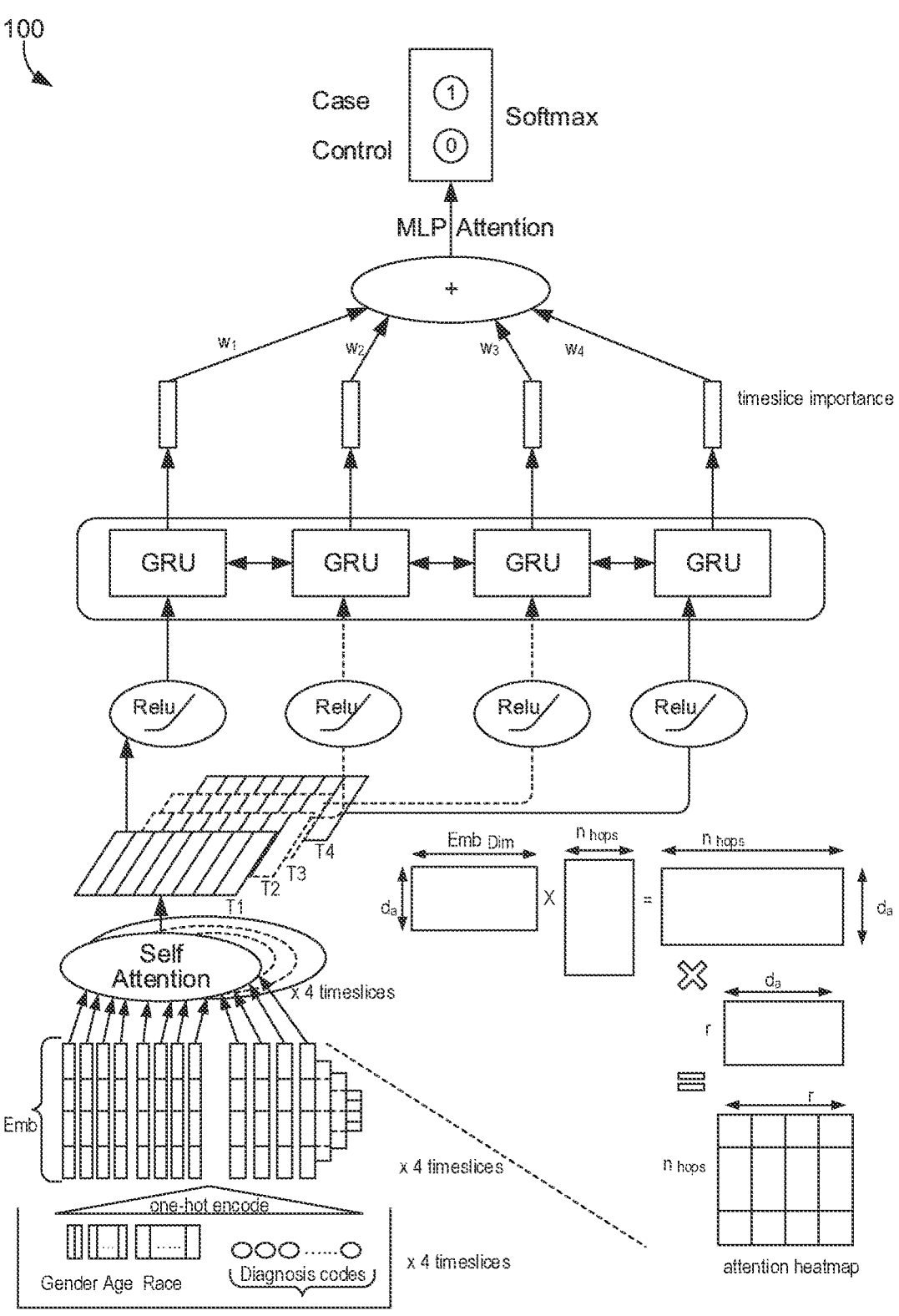
FIG. 1 illustrates a system architecture, in accordance with aspects.

The subject matter of the present invention is being described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Terms should not be interpreted as implying any particular order among or between various steps herein disclosed unless and except when the order of individual steps is explicitly described. As such, although the terms "step" and/or "block" may be used herein to connote different elements of system and/or methods, the terms should not be interpreted as implying any particular order and/or dependencies among or between various components and/or steps herein disclosed unless and except when the order of individual steps is explicitly described. The present disclosure will now be described more fully herein with reference to the accompanying drawings, which may not be drawn to scale and which are not to be construed as limiting. Indeed, the present invention can be embodied in many different forms and should not be construed as limited to the embodiments set forth herein.

As later discussed herein, a disease-agnostic data model is automatically generated based on a disease definition. The same disease-agnostic data model can be utilized to predict a time window for onset of multiple chronic diseases. Additionally, as further discussed herein, the aspects provide technological improvements over existing data models and existing techniques for creating data models because the aspects can identify features based on temporal changes in data across the observation window period for patients.

Aspects herein can predict a future time window and/or a future date at which point a specific patient is anticipated to experience the onset of chronic disease. The onset of chronic disease cannot be accurately performed by a clinician (e.g., disease onset predictions are currently a flat-out guess). Additionally, the onset of chronic disease cannot be accurately performed by existing computerized systems and data models, as well. For example, a future time window and/or a future date, at which point a specific patient is anticipated to experience the onset of chronic disease, is technologically challenging because electronic medical records (EMR) and electronic health records (EHR) include data that is difficult work with and analyze. Specifically, the data is complex and difficult to utilize due to: data heterogeneity, high dimensionality (e.g., there are over 14,000 codes in the ICD-9 terminology alone), data sparsity (low density), data irregularity, temporality, and bias. Thus, the ability to predict a future date and/or future date ranges at which point a specific patient is anticipated to experience the onset of chronic disease, and which cannot be performed manually or through existing methods, systems, and data models, is a technological improvement provided by aspects herein over existing manual methods and computerized systems and data models.

Beginning with FIG. 1, an example of a computerized system architecture is shown for generating and leveraging a disease-agnostic onset prediction model. In some aspects, the system 100 includes a first layer 102 that is an embedding layer, a second layer 104 that is a connected layer, and a recurrent neural network 106. The system 100 may include one or more processors (not shown), that operate to support the system 100 and are used to perform system functions. The system 100 may operate using one or more computing devices, such as the computing device 200 of FIG. 2, which may include one or more processors (not shown) that operate to support the system 100 and are used to perform system functions.

The system 100 can autonomously build, create, and/or generate a new data model using input information, and with little to no human interaction. In some aspects, the system 100 can generate a new data model that can be leveraged to predict a date or date range of onset of one or more chronic diseases for individual patients. In order to build, create, and/or generate a data model for chronic disease onset prediction, the system 100 and/or the computing device 200 accesses, obtains, retrieves and/or receives receiving electronic data that encodes longitudinal medical histories of a plurality of patients. Each longitudinal medical history is specific to a different particular patient, and each longitudinal medical history includes comprehensive patient-specific information for a defined time span, for example, from months to years in duration. Each longitudinal medical history may correspond to a different time duration (e.g., length of time: one history may include five years of information, while another history includes six months of information), or in relativity to other longitudinal medical histories (e.g., when: one history may include information for the years 1990 to 2010, while another history includes six months from the year 2018). Accordingly, each longitudinal medical history is unique to the patient to which the longitudinal medical history corresponds.

As such, in aspects, the longitudinal medical histories include patient information (e.g., address, medical record number), demographic information (e.g., race, gender, sex, age), medical encounter information (e.g., treating clinicians, appointments, clinical notes, prescriptions, procedures, laboratory results and values, images such as x-rays, magnetic resonance imaging (MRI) scans, positron emission tomography (PET) scan), and conditions information (e.g., diagnosis, staging, acute illness, chronic disease). Further, the longitudinal medical history for each patient includes one or more diagnosis codes and procedure codes, in various aspects. In one example, a portion of or all of the longitudinal medical histories may include one or more diagnosis codes for a chronic disease (e.g. one or more ICD-9 and/or ICD-10 codes for diabetes mellitus type 2, chronic heart failure, chronic obstructive pulmonary disease, and/or kidney failure) for those patients having been diagnosed with one or more chronic diseases. In a further example, a portion of the longitudinal medical histories may include one or more procedure codes for treatments that are specific to or correspond to treating a chronic disease for those patients having received treatments for one or more chronic diseases. Additionally or alternatively, for example, a portion of or all of the longitudinal medical histories may include one or more procedure codes for treatments that are specific to or correspond to treating a chronic disease for those patients having received treatments for one or more chronic diseases. In one aspect, particularly with regard to building the new data model, all of the longitudinal medical histories include at least one diagnosis code and/or procedure code that is associated with, corresponds to, and/or is specific to one particular chronic disease. In one aspect and particularly with regard to building the new data model, all of the longitudinal medical histories utilized may include at least one diagnosis code and/or procedure code that is associated with, corresponds to, and/or is specific to one particular chronic disease as well as two or more medical encounters occurring within a defined period of time relative to the code(s) associated with the particular chronic disease. In some aspects, the number and scale of the longitudinal medical histories utilized by the system 100 may vary from fifty or fewer records, up to millions of histories (i.e., histories may vary in size, volumes, bytes). As such, the system 100 discussed herein is both scalable and the longitudinal medical histories are not required to be uniform in format, size, time span, data compatibility, or content in order for the system 100 to autonomously build the new data model. In some aspects, the system 100 may map the electronic data (including the histories) to one or more standard nomenclatures or medical terminologies (e.g., ICD-9, ICD-10, SNOMED, and LOINC®), for example, and the system 100 may further match patients across disparate and incompatible data sources. In some further aspects, personal health information (PHI) may be automatically removed or scrubbed by the system 100 in compliance with medical and regulatory de-identification guidelines.

Before, after, or concurrently with receiving the electronic data that encodes the longitudinal medical histories of a plurality of patients, the system 100 and/or the computing device 200 receives an indication for a chronic disease. In various aspects, the chronic disease indicated may be diabetes mellitus type 2, chronic heart failure, chronic obstructive pulmonary disease, and/or kidney failure, for example, though other chronic diseases are contemplated to be within the scope of this disclosure. Accordingly, a user input or user selection may be received by the system 100 and the input or selection may identify, specify, and/or define a particular chronic disease. Based on the indication of the chronic disease, the system 100 can generate the new model to specifically predict a date or future date range in the future of onset of that particular chronic disease for each of the plurality of patients correspond to the longitudinal medical histories in the electronic data, as described hereinafter. For example, particularly with regard to building the new data model, the system may 100 may locate all of the longitudinal medical histories that at least one diagnosis code and/or procedure code that is associated with, corresponds to, and/or is specific to one particular chronic disease. In a further example, the system 100 may disregard the remainder of longitudinal medical histories that lack at least one diagnosis code and/or procedure code that is associated with, corresponds to, and/or is specific to one particular chronic disease of the indication. Using the indication of the chronic disease and the longitudinal medical histories, the system 100 can, as discussed herein, determine which patients have a reduced likelihood of experiencing onset of the particular chronic disease at a future date or future date range and which patients have an increased likelihood of experiencing the onset of the particular chronic disease at a future date or future date range, in various aspects. The likelihoods may be determined using the model to calculate probabilities, statistics, or other metrics, as discussed hereinafter.

The system 100 may automatically generate a plurality of distributions for a plurality of features that are present in the longitudinal medical histories of a plurality of patients encoded in the electronic data. In one aspect, the distribution component 202 of the computing device 200 of FIG. 2 may transform the electronic data into a plurality of feature-specific distributions. Features may include, for example, patient identifying information (e.g., name, address, medical record number), demographic information (e.g., race, gender, sex, age), medical encounter information (e.g., treating clinicians, appointments, clinical notes, prescriptions, procedures, laboratory results and values, images such as x-rays, magnetic resonance imaging (MRI) scans, positron emission tomography (PET) scan), and conditions information (e.g., diagnosis, staging, acute illness, chronic disease). Further, features may include, for example, diagnosis codes and procedure codes that are present in the electronic data.

In one example, one or more graphical distributions are created that include all of the patients that have a diagnosis code that is specific to the particular chronic within their respective longitudinal medical histories. In this example, the distributions may be analyzed to determine patterns of occurrence of specific individual features of patient identifying information, medical encounter information, conditions information, other diagnosis codes, procedure codes, and combinations thereof. Further, the patterns may evaluated relative to a known date of onset of the chronic disease that is encoded in the longitudinal medical histories of the plurality of patients, in such an example.

Figure 5:
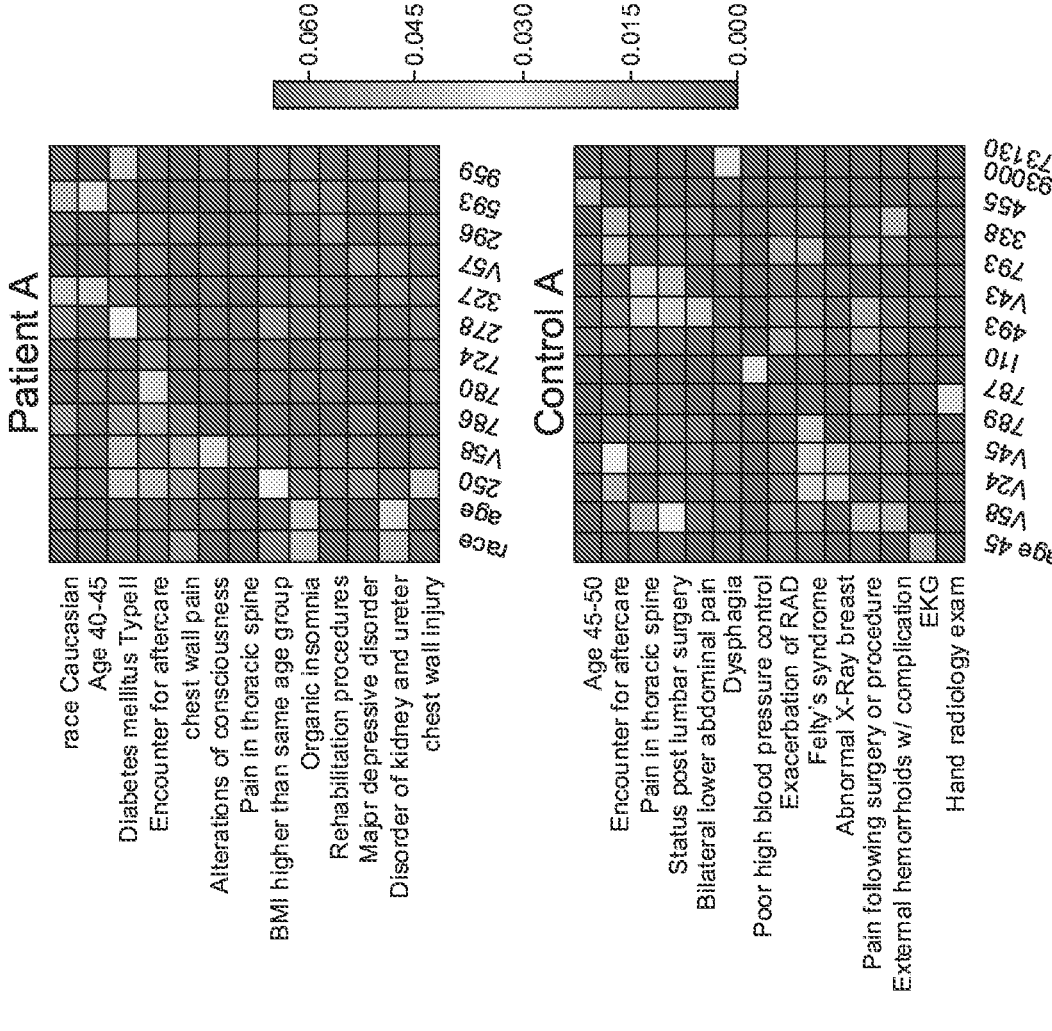
FIG. 5 depicts an example heat map of features correspondence to a chronic disease, in accordance with aspects.

The system 100 can automatically select, via one or more processors, two or more of the plurality of features from the distributions for use when building the new data model for predicting onset of the chronic disease. In various aspects, the two or more of the plurality of features are selected by the system 100 as corresponding to the particular chronic disease identified in the indication, and based on the distributions generated by the system 100. In one aspect, the distribution component 202 and/or the feature selection component 204 of the computing device 200 of FIG. 2 may automatically make the selection of a plurality of features to be used in building the model. Unlike current data modeling techniques, the system 100 is intelligent and can automatically identify and select features to be utilized in building the data model. FIG. 5 depicts an example of a heat map of features of one patient relative (e.g., having chronic disease onset) to a control patient (e.g., not having chronic disease onset). In FIG. 5, the shades of black and white indicate the co-occurrence (or absence) of features that are located on the y-axis relative to features on the x-axis. In one example, specific ICD-9 or ICD-10 codes can be selected as features for use in building the data model, when the system 100 determines those specific diagnosis and/or procedure codes correspond to and/or are present prior to onset of a chronic disease. As such, the system selects the specific diagnosis and/or procedure codes as potential predictors relative to the onset of a chronic disease, in some aspects.

Figure 6:
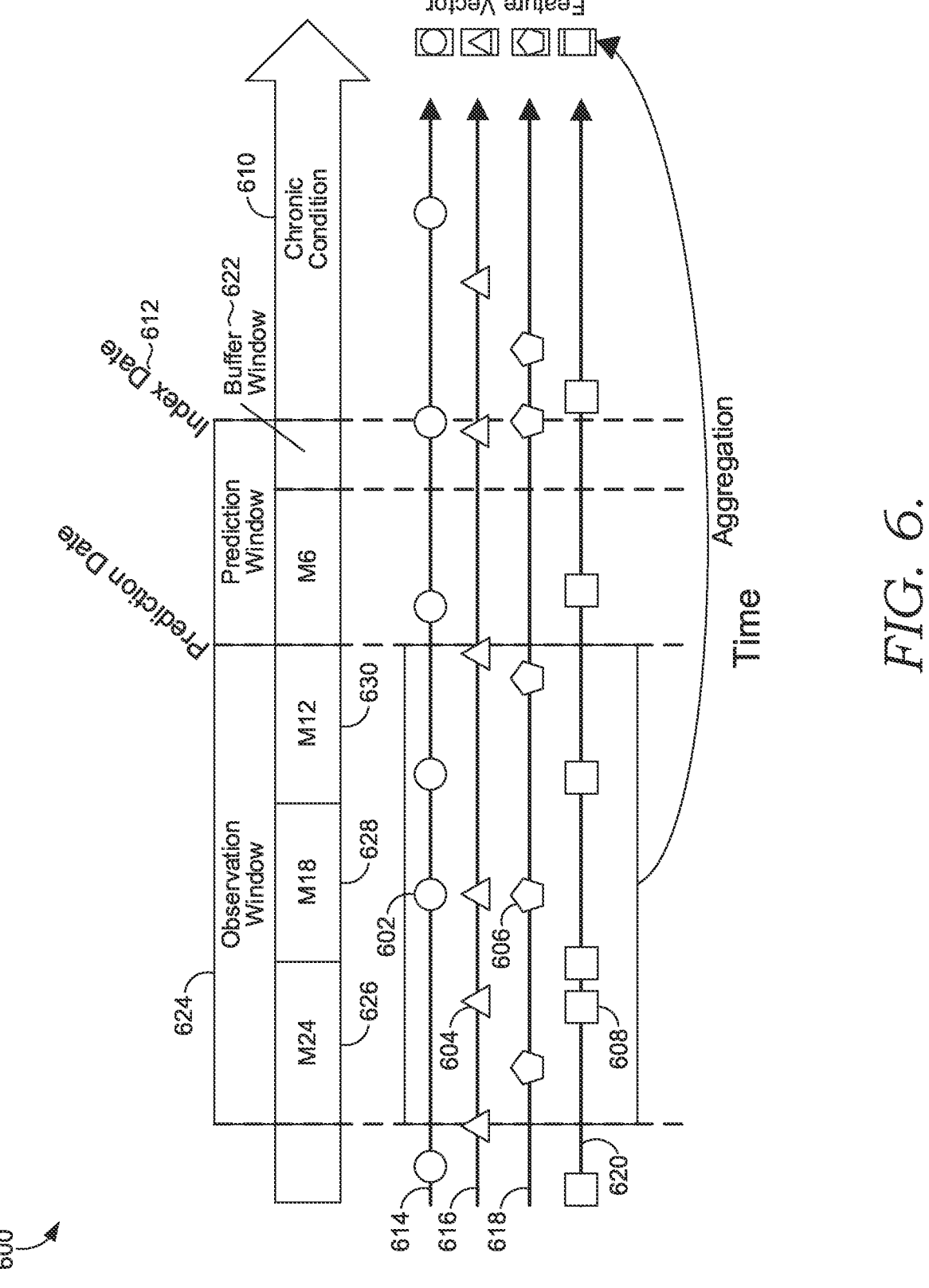
FIG. 6 depicts a graphic illustration of feature selection, in accordance with aspects.

After feature selection, the system 100 can embed a first plurality of vectors for the plurality of patients. The first plurality of vectors can include the two or more selected features. Further, the system 100 can embed a second plurality of vectors for a plurality of medical concepts identified in the electronic data encoding longitudinal medical histories of a plurality of patients. In one example, for each patient, the longitudinal medical history may be divided or apportioned into two or more time periods spanned by the longitudinal medical history (e.g., a longitudinal medical history spanning five years can be divided into ten different six-month time periods within the five years). As such, the longitudinal medical history of a patient may be apportioned into "time slices." In one example, the date of the first qualifying encounter with a diagnosis code or procedure code that is specific to the chronic disease is automatically selected by the system as an index date or known onset date of the chronic disease. In such an example, "time slices" are apportioned relative to the index date. A buffer time span before, after, or surrounding the index date may be selected and accounted for by the system 100 when apportioning the longitudinal medical history into multiple time slices that occur prior to the index date, in some embodiments. For example, FIG. 6 depicts a graphical illustration of feature selection. The graphical illustration depicts features 602, 604, 606, 608 that are being selected for a chronic condition 610, an index date 612 relative to which the longitudinal medical records 614, 616, 618, 620 are organized, a buffer window 622 preceding the index date 612, and an observation window 624 that is apportioned into time slices 626, 628, and 630 (e.g., 12 months, 18 months, 24 months) moving back in time from the index date 612 (and buffer window 622).

Figure 7:
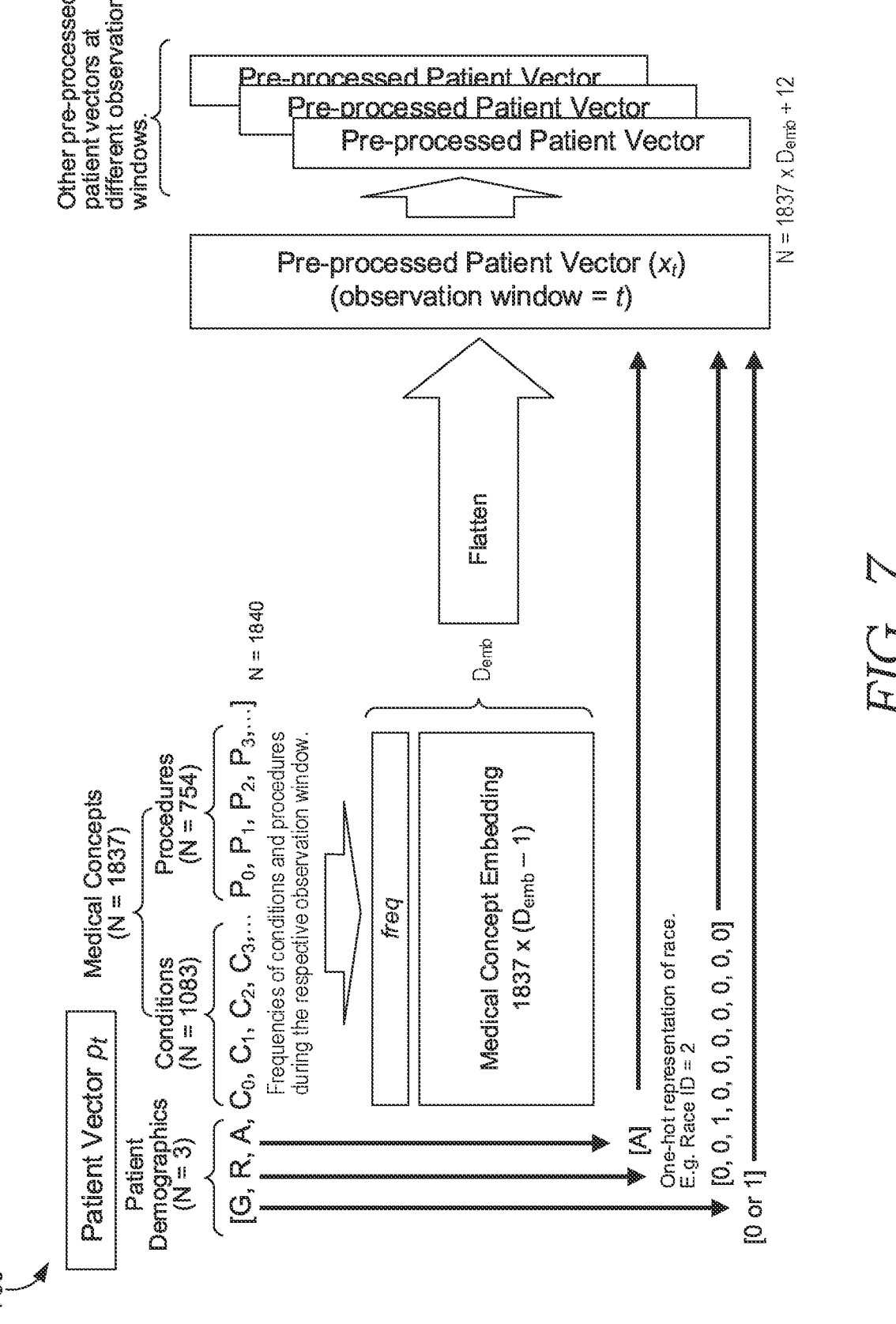
FIG. 7 illustrates a graphic representation of feature embedding using time slices, in accordance with aspects.

Features that include the patients gender or sex, race, and age may be embedded into first plurality of vectors, where each vector correspond to a different time slice, in aspects. Further, one or more diagnosis codes and/or procedure codes in the longitudinal medical history of a patient may be embedded into the second plurality of vectors, where each vector correspond to a different time slice. In one example, the first plurality of vectors may then be concatenated to the second plurality of vectors by pairing the vectors that correspond to respective time slices, in order to generate comprehensive patient vectors for each time slice in the longitudinal medical history for that patient, as discussed hereinafter. FIG. 1 illustrates the first layer 102 that is an embedding layer in the system architecture for performance of these embedding actions. Additionally, the embedding component 206 of the computing device 200 in FIG. 2 may be used to perform any and all of the embedding tasks via the first layer 102 of the system 100. In further aspects, the embedding component 206 and/or the recurrent neural network component 208 may work in tandem or serially to concatenate each of the first plurality of vectors with one of the second plurality of vectors to generate a patient-specific input vector for each patient of the plurality of patients. FIG. 7 illustrates a graphic representation of how features may be embedded into vectors for each patient and the time slices of the longitudinal medical history of the patient, for each of the patients in the plurality, in some aspects.

Continuing, the system 100 may process the first and second plurality of vectors (e.g., as concatenated together for a time slice) using the recurrent neural network component 208 of FIG. 2 and/or the recurrent neural network 106 of FIG. 1. Processing can include aligning sequential observation time periods (i.e., time slices) of the longitudinal medical histories relative to known dates of onset (i.e., index dates) of the chronic disease for two or more of the plurality to patients. Then, the system 100 may output, from the recurrent neural network 106, a disease-agnostic onset prediction model based on the first and second plurality of vectors as processed by the recurrent neural network. In one aspect, the recurrent neural network component 208 of the computing device 200 in FIG. 2 outputs the disease-agnostic onset prediction model. As such, the system 100 may build the data model, and the aforementioned functions performed by the system 100 may be repeated for one or more different chronic diseases, in some aspects.

To illustrate the system functions discussed above, an example follows with regard to techniques for embedding. In one example, at least a portion of demographic information extracted from the longitudinal medical history of a patient, such as age $A_i$, may be converted into categorical features by binning, while another portion of demographic information of that patient, including features such as race $R_i$ and gender (sex) $G_i$, may be integer encoded. A final feature representation $$F_i^t$$

for the one patient for any given time slice from the longitudinal medical record may be determined by concatenating the representations of all the selected features (e.g., the first and second plurality of vectors) into a single patient-specific and time-slice specific vector $$[G_i, R_i, A_i, h_i^t],$$

where $$h_i^t$$

represents homogeneous feature representation for patient i in time slice t, where the length is represented as n, in this example. The final feature representation $$F_i^t$$

can be passed through the first layer 102 that is an embedding layer, in one such example. Each feature may be embedded, represented by E of n×e, where e is an embedding dimension, in an example. A self-attention may also be employed, such that, for example, the second layer 104 in the system 100 is a fully connected layer that includes self-attention. In such an example, attention may be determined for each of the features relative to the other features included in the final feature representation $$F_i^t$$

via E. The self-attention layer may be used to create the single patient-specific and time-slice specific vector having weights a, where $w_{s1}$ is a weight matrix with a shape of $d_a \times e$ and where $w_{s2}$ is a vector of parameters with size $d_a$. To capture complex feature-to-feature interactions for the final feature representation $$F_i^t,$$

multiple hops of attention may be employed, in one example. Further, to extract r different parts from $F_{Ht}$, the vector $w_{s2}$ may be expanded into a matrix of $r \times d_a$, which may be denoted as $W_{s2}$. In this example, the annotation vector a and annotation matrix A may be represented as:

$$a = \text{softmax}(w_{s2} \tan h(w_{s1}E^T))$$

$$A = \text{softmax}(W_{s2} \tan h(W_{s1}E^T))$$

Further still, r weighted sums may be determined by multiplying the annotation matrix A with the embedding output E matrix, resulting in $$Q_i^t = AE.$$

In this example, longitudinal dependencies between the features are determined, leveraged, and weighted for the corresponding patient in vectorizing the longitudinal medical history. The embedded vectors may be transferred from the second layer 104 to the recurrent neural network 106 in the system 100. In some aspects, the recurrent neural network may be a Long Short-Term Memory (LSTM) type of recurrent neural network or a bidirectional Gated recurrent units (GRU) type recurrent neural network layer, for example.

Continuing, having built a new data model for predicting onset of one or more different chronic diseases, the system 100 may leverage the model over and over again, to predict the onset of multiple chronic diseases based on the system 100 selecting new features for a different chronic disease and performing the embedding and processing discussed above. In this manner, a disease-agnostic data model is built that can be leveraged to predict the onset of various chronic diseases for patients.

For example, the system 100 may receive new electronic data encoding longitudinal medical histories of a plurality of patients to be evaluated using the disease-agnostic data model and the system 100 may access the disease-agnostic onset prediction model. The system 100 may receive an indication that identifies a chronic disease for the evaluation. Using the chronic disease that is indicated, the system 100 may select, via one or more processors, two or more features of the longitudinal medical histories that are identified by the disease-agnostic onset prediction model as being predictors of the chronic disease (i.e., selection without additional user input or manual input). In one aspect, the feature selection component 204 of the computing device 200 in FIG. 2 is used by the system 100 to select specific features. The system 100 may, via the embedding component 206 of the first layer 102, embed the electronic data encoding the longitudinal medical histories using the disease-agnostic onset prediction model to generate a plurality of vectors for the plurality of patients, in some aspects. Each of the plurality of vectors includes values for the two or more features from the electronic data for one of the plurality of patients. The system 100 may continue by processing the plurality of vectors for the plurality of patients using the recurrent neural network 106 and the recurrent neural network component 208. Then, the system 100 may output, from the recurrent neural network 106 and using the prediction component 210, a predicted onset time period for the chronic disease for at least one of the plurality of patients. In other terms, the system 100 can predict a future date and/or a future date range during which a particular patient is anticipated to (or is not anticipated to) experience the onset of the chronic condition.

Figure 3:
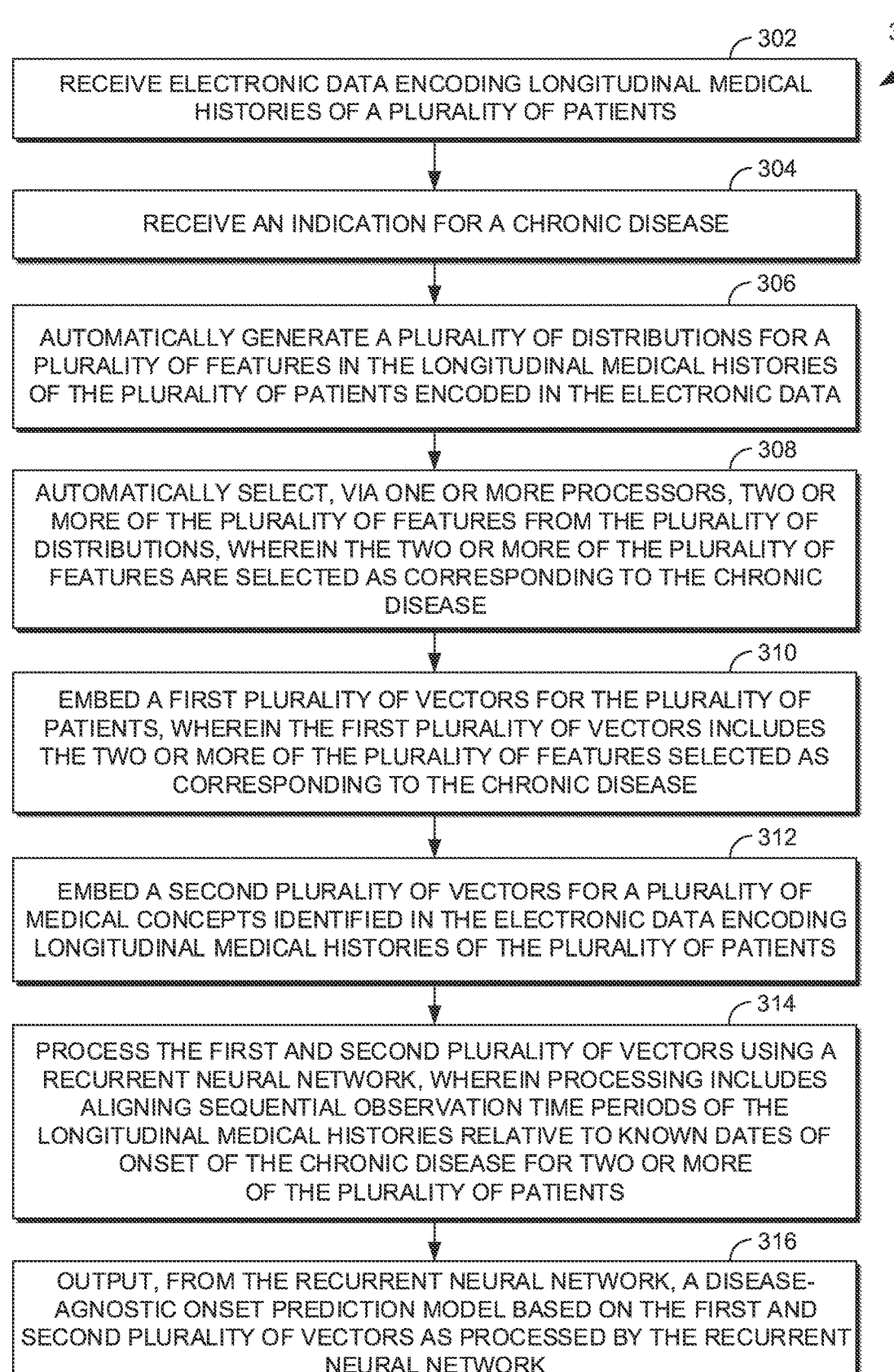
FIG. 3 depicts a method for automated generation of a disease-agnostic onset prediction model, in accordance with aspects.

Turning now to FIGS. 3 and 4, methods are discussed that can be performed via one or more of the devices, components, and/or component interactions previously described in FIGS. 1 and 2. It should be understood that the methods discussed herein can be implemented or performed via the execution of non-transitory computer-readable instructions and/or executable program code portions stored on computer readable media, using one or more processors. The computer-readable program code can correspond to the application, described above, wherein the application performs the methods, in some aspects. In aspects, the methods can be implemented and performed using a computerized application. As such, the methods can be computer-implemented methods, in some aspects, integrated with and executed to complement a computerized clinical workflow.

FIG. 3 illustrates a flowchart of a method 300 for automated generation of a disease-agnostic onset prediction model. At block 302, electronic data that encodes longitudinal medical histories of a plurality of patients is received. At block 304, an indication for a chronic disease is received. In one aspect, the indication identifies, specifies, or defines the chronic disease as one of diabetes mellitus type 2, chronic heart failure, chronic obstructive pulmonary disease, or kidney failure. At block 306, a plurality of distributions are automatically generated for a plurality of features in the longitudinal medical histories. At block 308, two or more of the plurality of features are automatically selected from the distributions, where the two or more of the plurality of features are selected as corresponding to the chronic disease via one or more processors. At block 310, a first plurality of vectors is embedded for the plurality of patients, and the first plurality of vectors includes the two or more of the plurality of features selected as corresponding to the chronic disease. In one aspect, each of the first plurality of vectors further includes gender, age, and race that are present in the electronic data specific to one of the plurality of patients. Additionally or alternatively, each of the first plurality of vectors further includes one or more diagnosis codes and procedure codes that are present in the electronic data specific to one of the plurality of patients. Embedding the first plurality of vectors can include flattening values for the two or more features from one or more sequential observation time periods in the longitudinal medical histories, in some aspects. At block 312, a second plurality of vectors is embedded for a plurality of medical concepts identified in the electronic data encoding the longitudinal medical histories of the plurality of patients. In one aspect, the second plurality of vectors includes one or more diagnosis codes and procedure codes that are present in the electronic data encoding longitudinal medical histories of the plurality of patients. Additionally or alternatively, the second plurality of vectors includes a frequency for one or more diagnosis codes and procedure codes that are present in the electronic data, in some aspects. In one aspect, embedding the second plurality of vectors includes flattening one or more medical concepts from the longitudinal medical histories. The second plurality of vectors can include features of one or more of medications, allergies, care plans, provider appointments, and questionnaire information, in some aspects.

At block 314, the first and second plurality of vectors are processed using a recurrent neural network, and processing includes aligning sequential observation time periods of the longitudinal medical histories relative to known dates of onset of the chronic disease for two or more of the plurality to patients. In one aspect, the recurrent neural network includes a long short-term memory recurrent network. Processing the first and second plurality of vectors using the recurrent neural network can include, in some aspects, concatenating each of the first plurality of vectors with one of the second plurality of vectors to generate a patient-specific input vector for each patient of the plurality of patients. In such aspects, for each individual patient, a concatenated vector is generated for each of multiple time slices by apportioning corresponding electronic data in the longitudinal medical history, such that each patient is represented by a vector for each time slice. At block 316, a disease-agnostic onset prediction model is output from the recurrent neural network's processing of the first and second plurality of vectors.

Turning to FIG. 4, a method 400 is provided for automatically predicting patient onset of chronic disease based on a disease-agnostic onset prediction model. At block 402, electronic data encoding longitudinal medical histories of a plurality of patients is received. At block 404, a disease-agnostic onset prediction model is accessed. In some aspects, the disease-agnostic onset prediction model generated through the method 300 of FIG. 3 is accessed. At block 406, an indication that identifies a chronic disease is received. In various aspects, the chronic disease is one of diabetes mellitus type 2, chronic heart failure, chronic obstructive pulmonary disease, or kidney failure. At block 408, two or more features of the longitudinal medical histories are selected by a processor based on the disease-agnostic onset prediction model, wherein the two or more features are autonomously selected, by the disease-agnostic onset prediction model, as being predictors of the chronic disease.

At block 410, the electronic data encoding the longitudinal medical histories is embedded using the disease-agnostic onset prediction model to generate a plurality of vectors for the plurality of patients, and each of the plurality of vectors includes values for the two or more features from the electronic data for one of the plurality of patients. In one example, a null value is used to generate a vector for a patient when the patient's longitudinal medical history does not include or exhibit a first feature of high blood pressure, while a positive value may be used to generate the same vector for the same patient when the patient's longitudinal medical history does include or exhibits the second feature of obesity. The plurality of vectors may be embedded using the same techniques previously described above that were used to create the disease-agnostic data model, however, this cohort of patients does not include a known onset date (e.g., index date) for the chronic disease such that the data model is being used to make such as prediction.

In some aspects, each of the plurality of vectors is a patient-specific vector that includes a gender, an age, and a race that are present in the electronic data specific to one of the plurality of patients. Additionally, in various aspects, each of the plurality of vectors further includes a frequency of one or more diagnosis codes and procedure codes that are present in the electronic data specific to one of the plurality of patients. Generally, each of the plurality of vectors corresponds to the electronic data for a different time period for one of the plurality of patients. Accordingly, a plurality of vectors representing different time slices are embedded for each individual patient, for the purpose of predicting onset. The plurality of vectors may be embedded using the same techniques previously described above that were used to create the disease-agnostic data model, in aspects.

At block 412, the plurality of vectors for the plurality of patients is processed using a recurrent neural network. In one aspect, the recurrent neural network is a long short-term memory recurrent network. In some aspects, the plurality of vectors are processed by, for each patient, comparing the two or more features in the first plurality of vectors to the two or more features temporally associated with onset for the chronic disease in the disease-agnostic onset prediction model. In one such aspect, a future time period is determined for at least one of the plurality of patients, where the future time period is associated with a greatest likelihood of onset of the chronic disease for that at least one particular patient based on comparing the two or more features. The estimated future time period can be identified as, defined as, and/or designated as, in some aspects, the predicted onset time period for the chronic disease for that particular patient in the plurality of patients. Accordingly, a predicted onset time period may be identified for each one or more individual patients in the plurality of patients, wherein each predicted onset time is unique to and specific to each individual patient, based on the patient-specific vectors processed using the recurrent neural network and the disease-agnostic model.

At block 414, a predicted onset time period for the chronic disease for at least one of the plurality of patients is output from the recurrent neural network. Further, the predicted onset time may be caused to be displayed in a graphical user interface, wherein the predicted onset time includes a date or ranges of dates.

Beginning with FIG. 8, a computing environment 800 that is suitable for use in implementing aspects of the present invention is depicted. The computing environment 800 is merely an example of one suitable computing environment and is not intended to suggest any limitation as to the scope of use or functionality of the invention. Neither should the computing environment 800 be interpreted as having any dependency or requirement relating to any single component or combination of components illustrated therein. Generally, in aspects, the computing environment 800 is a medical-information computing-system environment.

However, this is just one example and the computing environment 800 can be operational with other types, other kinds, or other-purpose computing system environments or configurations. Examples of computing systems, environments, and/or configurations that might be suitable for use with the present invention include personal computers, server computers, hand-held or laptop devices, multiprocessor systems, microprocessor-based systems, set top boxes, programmable consumer electronics, network PCs, mini-computers, mainframe computers, distributed computing environments that include any of the above-mentioned systems or devices, and the like.

In aspects, the computing environment 800 can be described in the general context of computer instructions, such as program modules, applications, and/or extensions, being read and executed by a computing device. Examples of computer instructions can include routines, programs, objects, components, and/or data structures that perform particular tasks or implement particular abstract data types. The aspects discussed herein can be practiced in centralized and/or distributed computing environments, i.e., where computer tasks are performed utilizing remote processing devices that are linked through a communications network, whether hardwired, wireless, or a combination thereof. In a distributed configuration, computer instructions might be stored or located in association with one or more local and/or remote computer storage media (e.g., memory storage devices). Accordingly, different portions of computer instructions for implementing the computer tool in the computing environment 800 may be executed and run on different devices, whether local, remote, stationary, and/or mobile.

With continued reference to FIG. 8, the computing environment 800 comprises a computing device 802, shown in the example form of a server. Although illustrated as one component in FIG. 8, the present invention can utilize a plurality of local servers and/or remote servers in the computing environment 800. The computing device 802 can include components such as a processing unit, internal system memory, and a suitable system bus for coupling to various components, including electronic storage, memory, and the like, such as a data store, a database, and/or a database cluster. Example components of the computing device 802 include a processing unit, internal system memory, and a suitable system bus for coupling various components, including a data store 804, with the computing device 802. An example system bus might be any of several types of bus structures, including a memory bus or memory controller, a peripheral bus, and a local bus, using any of a variety of bus architectures. Examples of bus architectures include Industry Standard Architecture (ISA) bus, Micro Channel Architecture (MCA) bus, Enhanced ISA (EISA)

bus, Video Electronic Standards Association (VESA) local bus, and Peripheral Component Interconnect (PCI) bus, also known as Mezzanine bus.

The computing device 802 includes or has access to a variety of non-transitory computer-readable media. Computer-readable media can be any available media that is locally and/or remotely accessible by the computing device 802, and includes volatile, nonvolatile, removable, and non-removable media. By way of example, and not limitation, computer-readable media can comprise computer storage media and communication media. Computer storage media includes volatile, nonvolatile, removable, and non-removable media, as implemented in any method or technology for storage of information, such as computer-readable instructions, data structures, program modules, or other data.

The computing device 802 can include or can have access to computer-readable media. Computer-readable media can be any available media that can be accessed by computing device 802, and includes volatile and nonvolatile media, as well as removable and non-removable media. By way of example, and not limitation, computer-readable media can include computer storage media and communication media.

Computer storage media can include, without limitation, volatile and nonvolatile media, as well as removable and non-removable media, implemented in any method or technology for storage of information, such as computer-readable instructions, data structures, program modules, or other data. In this regard, computer storage media can include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which can be accessed by the computing device 802. Computer storage media does not comprise signals per se.

Communication media typically embodies computer-readable instructions, data structures, program modules, or other data in a modulated data signal, such as a carrier wave or other transport mechanism, and can include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also can be included within the scope of computer-readable media.

The computing device 802 might operate in a network 806 using logical connections to one or more remote computers 808. In some aspects, the one or more remote computers 108 can be located at a variety of locations, such as medical facilities, research environments, and/or clinical laboratories (e.g., molecular diagnostic laboratories), as well as hospitals, other inpatient settings (e.g., surgical centers), veterinary environments, ambulatory settings, medical billing offices, financial offices, hospital administration settings, home healthcare environments, and/or clinicians' offices). As used herein, "clinicians," "medical professionals," or "healthcare providers" can include: physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like.

In aspects, the computing device 802 uses logical connections to communicate with one or more remote computers 808 within the computing environment 800. In aspects where the network 806 includes a wireless network, the computing device 802 can employ a modem to establish communications with the Internet, the computing device 802 can connect to the Internet using Wi-Fi or wireless access points, or the server can use a wireless network adapter to access the Internet. The computing device 802 engages in two-way communication with any or all of the components and devices illustrated in FIG. 8, using the network 806. Accordingly, the computing device 802 can send data to and receive data from the remote computers 808 over the network 806.

The network 806 is a computer network that can include local area networks (LANs) and/or wide area networks (WANs), in some aspects. The network 806 can include wireless and/or physical (e.g., hardwired) connections. Examples of networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. When the network 806 includes a WAN-type configuration, the computing device 802 might comprise a modem or other means for establishing communications over the WAN, such as the Internet, in such aspects. As such, the network 806, can provide the components and devices access to the Internet and web-based applications.

The network 806 can include an entity-wide network, campus-wide network, an office-wide network, an enterprise-wide networks, and the Internet. In the network 806, applications, extensions, program modules or portions thereof might be stored in association with the computing device 802, the data store 804, and any of the one or more remote computers 808. For example, various application programs can reside on the memory associated with any one or more of the remote computers 808. In the computing environment 800, which is illustrated as being a distributed configuration of the network 806, the components and devices can communicate with one another and can be linked to each other using a network 806. It will be appreciated by those of ordinary skill in the art that the network connections shown are exemplary and other means of establishing a communications link between the computers (e.g. computing device 802 and remote computers 808) might be utilized.

In operation, an organization might enter commands and information into the computing device 802 or convey the commands and information, for example, directly in peer-to-peer or near-field communication, or through the network 806 using telecommunications or Wi-Fi, to the computing device 802 via one or more of the remote computers 808 through input devices, such as a keyboard, a pointing device (e.g., a mouse), a trackball, as stylus, or a touch pad. Other input devices comprise microphones, satellite dishes, scanners, or the like. Commands and information might also be sent directly from a remote healthcare device to the computing device 802. In addition to a screen, monitor, or touchscreen component, the computing device 802 and/or remote computers 808 might comprise other peripheral output devices, such as speakers and printers.

The computing environment 800 includes one or more remote computers 808, which may be accessed by the computing device 802 over the network 806 or directly using peer-to-peer connections or mesh networking, in various aspects. The remote computers 808 might be servers, routers, network personal computers, peer devices, network nodes, computing devices, personal digital assistants, personal mobile devices, medical devices, patient monitoring equipment, or the like, and might comprise some or all of the elements described above in relation to the computing device 802. The one or more remote computers 808 can include multiple computing devices, in various aspects. In aspects where the network 806 is distributed in configuration, the one or more remote computers 808 can be located at one or more different geographic locations. In an aspect where the one or more remote computers 808 are a plurality of computing devices, each of the plurality of computing devices can be located across various locations such as buildings in a campus, medical and research facilities at a medical complex, offices or "branches" of a banking/credit entity, or can be mobile devices that are wearable or carried by personnel, or attached to vehicles or trackable items in a warehouse, for example. In some aspects, the remote computers 808 are physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. The remote computers 108 might also be physically located in nontraditional healthcare environments so that the entire healthcare community might be capable of integration on the network 806. In other aspects, the remote computers 108 can be physically located in a non-medical setting, such as a packing and shipping facility or deployed within a fleet of delivery or courier vehicles.

Continuing, the computing environment 800 includes a data store 804. Although shown as a single component, the data store 804 can be implemented using multiple data stores that are communicatively coupled to one another, independent of the geographic or physical location of a memory device. The data store 804 can, for example, store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. The data store 804 can, for example, also store data in the form of electronic records, such as electronic medical records of patients, patient-specific documents and historical records, transaction records, billing records, task and workflow records, chronological event records, and the like. Generally, the data store 804 includes physical memory that is configured to store information encoded in data. For example, the data store 804 can provide storage for computer-readable instructions, computer-executable instructions, data structures, data arrays, computer programs, applications, and other data that supports the functions and actions to be undertaken using the computing environment 800 and components shown in the example of FIG. 8.

As shown in the example of FIG. 8, when the computing environment 800 operates with distributed components that are communicatively coupled via the network 806, computer instructions, applications, extensions, and/or program modules can be located in local and/or remote computer storage media (e.g., memory storage devices). Aspects of the present invention can be described in the context of computer-executable instructions, such as program modules, being executed by a computing device. Program modules can include, but are not limited to, routines, programs, objects, components, and data structures that perform particular tasks or implement particular abstract data types. In aspects, the computing device 802 can access, retrieve, communicate, receive, and update information stored in the data store 804, including program modules. Accordingly, the computing device 802 can execute, using a processor, computer instructions stored in the data store 804 in order to perform aspects described herein.

Although internal components of the devices in FIG. 8, such as the computing device 802, are not illustrated, those of ordinary skill in the art will appreciate that internal components and their interconnection are present in the devices of FIG. 8. Accordingly, additional details concerning the internal construction device are not further disclosed herein. Although many other internal components of the computing device 802 and the remote computers 808 are not shown, such components and their interconnection are known. Accordingly, additional details concerning the internal construction of the computing device 802 and the remote computers 808 are not further disclosed herein.

Additionally, it will be understood by those of ordinary skill in the art that the computing environment 800 is just one example of a suitable computing environment and is not intended to limit the scope of use or functionality of the present invention. Similarly, the computing environment 800 should not be interpreted as imputing any dependency and/or any requirements with regard to each component and combination(s) of components illustrated in FIG. 8. It will be appreciated by those having ordinary skill in the art that the connections illustrated in FIG. 8 are also examples as other methods, hardware, software, and devices for establishing a communications link between the components, devices, systems, and entities, as shown in FIG. 8, can be utilized in implementation of the present invention. Although the connections are depicted using one or more solid lines, it will be understood by those having ordinary skill in the art that the example connections of FIG. 8 can be hardwired or wireless, and can use intermediary components that have been omitted or not included in FIG. 8 for simplicity's sake. As such, the absence of components from FIG. 8 should be not be interpreted as limiting the present invention to exclude additional components and combination(s) of components. Moreover, though devices and components are represented in FIG. 8 as singular devices and components, it will be appreciated that some aspects can include a plurality of the devices and components such that FIG. 8 should not be considered as limiting the number of a device or component.

Regarding FIGS. 1 through 8, it will be understood by those of ordinary skill in the art that the environment(s), system(s), and/or methods(s) depicted are not intended to limit the scope of use or functionality of the present embodiments. Similarly, the environment(s), system(s), and/or methods(s) should not be interpreted as imputing any dependency and/or any requirements with regard to each component, each step, and combination(s) of components or step(s) illustrated therein. It will be appreciated by those having ordinary skill in the art that the connections illustrated the figures are contemplated to potentially include methods, hardware, software, and/or other devices for establishing a communications link between the components, devices, systems, and/or entities, as may be utilized in implementation of the present embodiments. As such, the absence of component(s) and/or steps(s) from the figures should be not be interpreted as limiting the present embodiments to exclude additional component(s) and/or combination(s) of components. Moreover, though devices and components in the figures may be represented as singular devices and/or components, it will be appreciated that some embodiments can include a plurality of devices and/or components such that the figures should not be considered as limiting the number of a devices and/or components.

It is noted that embodiments of the present invention described herein with reference to block diagrams and flowchart illustrations. However, it should be understood that each block of the block diagrams and/or flowchart illustrations can be implemented in the form of a computer program product, an entirely hardware embodiment, a combination of hardware and computer program products, and/or apparatus, systems, computing devices/entities, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code can be performed sequentially such that one instruction is retrieved, loaded, and executed at a time. In some embodiments, retrieval, loading, and/or execution can be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

Additionally, as should be appreciated, various embodiments of the present disclosure described herein can also be implemented as methods, apparatus, systems, computing devices/entities, computing entities, and/or the like. As such, embodiments of the present disclosure can take the form of an apparatus, system, computing device, computing entity, and/or the like executing instructions stored on a computer-readable storage medium to perform certain steps or operations. However, embodiments of the present disclosure can also take the form of an entirely hardware embodiment performing certain steps or operations.

Many different arrangements of the various components depicted, as well as components not shown, are possible without departing from the scope of the claims below. Embodiments of our technology have been described with the intent to be illustrative rather than restrictive. Alternative embodiments will become apparent readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A computerized method performed by one or more hardware processors of a medical-information computing system, the computerized method comprising:

accessing electronic data that includes a plurality of encoded longitudinal medical histories, the plurality of encoded longitudinal medical histories being created from clinical data extracted from a corresponding plurality of electronic health records, and each record of the plurality of electronic health records including (a) a defined time span associated with the record and (b) comprehensive record-specific information for the defined time span associated with the record;

receiving, via the one or more hardware processors, an indication for a chronic disease associated with at least a portion of: the defined time spans and the comprehensive record-specific information from which the plurality of encoded longitudinal medical histories are created;

in response to the receiving of the indication via the one or more hardware processors, automatically performing by the one or more hardware processors and without user input:

(a) generating a plurality of distributions for a plurality of features in the plurality of encoded longitudinal medical histories; and (b) selecting, via the one or more hardware processors and without user input, two or more of the plurality of features from the plurality of distributions, wherein the one or more hardware processors are associated with an electronic memory of the medical-information computing system, and wherein the two or more of the plurality of features are selected as corresponding to the chronic disease;

generating an onset time period for the chronic disease, the onset time period for the chronic disease being generated (a) for a particular longitudinal medical history of the plurality of encoded longitudinal medical histories associated with the chronic disease, (b) based on a first plurality of vectors for the plurality of encoded longitudinal medical histories, and (c) based further on a recurrent neural network, wherein: the first plurality of vectors includes the two or more of the plurality of features selected from the plurality of distributions as corresponding to the chronic disease, the recurrent neural network is configured using input data that is based on input vectors of data corresponding to instances of information selected from a group comprising longitudinal medical history data, the first plurality of vectors, and chronic disease indication data, the recurrent neural network is further configured based on aligning sequential observation time periods of longitudinal medical histories relative to known dates of onset of the chronic disease for two or more of the plurality of encoded longitudinal medical histories, and an instance of the input data associated with the particular longitudinal medical history is input to the recurrent neural network to produce output prediction data indicating the onset time period for the chronic disease; and presenting, via an electronic interface and based on at least the output prediction data, the onset time period for the chronic disease, wherein presenting the onset time period for the chronic disease includes communicating via the one or more hardware processors and via the electronic interface a date or a range of dates associated with the onset time period for the chronic disease.

2. The computerized method of claim 1, wherein the onset time period is generated based further on a second plurality of vectors for a plurality of medical concepts identified in the electronic data, by concatenating each of the first plurality of vectors with one of the second plurality of vectors to generate a specific vector for each longitudinal medical history of the plurality of encoded longitudinal medical histories.

3. The computerized method of claim 1, wherein the computerized method is performed via multiple hardware processors at different geographic locations associated with a distributed memory of the medical-information computing system, and wherein generating the plurality of distributions and selecting the two or more of the plurality of features are performed autonomously by the one or more hardware processors.

4. The computerized method of claim 1, wherein generating the onset time period is performed via the one or more hardware processors at:

an embedding layer of the medical-information computing system, in combination with a self-attention layer of the medical-information computing system, in combination with a recurrent neural network layer of the medical-information computing system.

5. One or more non-transitory media having instructions which, when executed by one or more hardware processors of a medical-information computing system, cause the one or more hardware processors to perform a plurality of operations, the operations comprising:

accessing electronic data that includes a plurality of encoded longitudinal medical histories, the plurality of encoded longitudinal medical histories being created from clinical data extracted from a corresponding plurality of electronic health records, and each record of the plurality of electronic health records including (a) a defined time span associated with the record; and (b) comprehensive record-specific information for the defined time span associated with the record;

receiving, via the one or more hardware processors, an indication for a chronic disease associated with at least a portion of: the defined time spans and the comprehensive record-specific information from which the plurality of encoded longitudinal medical histories are created;

in response to the receiving of the indication via the one or more hardware processors, automatically performing by the one or more hardware processors and without user input:

(a) generating a plurality of distributions for a plurality of features in the plurality of encoded longitudinal medical histories; and (b) selecting, via the one or more hardware processors and without user input, two or more of the plurality of features from the plurality of distributions, wherein the one or more hardware processors are associated with an electronic memory of the medical-information computing system, and wherein the two or more of the plurality of features are selected as corresponding to the chronic disease;

generating an onset time period for the chronic disease, the onset time period for the chronic disease being generated (a) for a particular longitudinal medical history of the plurality of encoded longitudinal medical histories associated with the chronic disease, (b) based on a first plurality of vectors for the plurality of encoded longitudinal medical histories, and (c) based further on a recurrent neural network, wherein: the first plurality of vectors includes the two or more of the plurality of features selected from the plurality of distributions as corresponding to the chronic disease, the recurrent neural network is configured using input data that is based on input vectors of data corresponding to instances of information selected from a group comprising longitudinal medical history data, the first plurality of vectors, and chronic disease indication data, the recurrent neural network is further configured based on aligning sequential observation time periods of longitudinal medical histories relative to known dates of onset of the chronic disease for two or more of the plurality of encoded longitudinal medical histories, and an instance of the input data associated with the particular longitudinal medical history is input to the recurrent neural network to produce output prediction data indicating the onset time period for the chronic disease; and presenting, via an electronic interface and based on at least the output prediction data, the onset time period for the chronic disease, wherein presenting the onset time period for the chronic disease includes communicating via the one or more hardware processors and via the electronic interface a date or a range of dates associated with the onset time period for the chronic disease.

6. The one or more non-transitory media of claim 5, wherein each of the first plurality of vectors corresponds to the electronic data for a different time period for one of the plurality of encoded longitudinal medical histories.

7. The one or more non-transitory media of claim 5, wherein operations further comprise, for each individual:

comparing two or more features in the first plurality of vectors to two or more features temporally associated with onset for the chronic disease in a disease-agnostic onset prediction model;

determining a future time period for the at least one of the plurality of encoded longitudinal medical histories, the future time period being associated with a greatest likelihood of onset of the chronic disease for the at least one of the plurality of encoded longitudinal medical histories based on the comparing; and identifying the future time period as the onset time period for the chronic disease for the at least one of the plurality of encoded longitudinal medical histories.

8. The one or more non-transitory media of claim 7, wherein the operations further comprise electronically writing the onset time period to a memory associated with the medical-information computing system, and wherein the onset time period includes a date and a range of dates.

9. The one or more non-transitory media of claim 5, wherein the operations further comprise updating the recurrent neural network based on information associated with additional instances of the data.

10. The one or more non-transitory media of claim 5, wherein configuring the recurrent neural network is based at least in part on a process selected from a group comprising supervised machine learning, reinforcement machine learning, and unsupervised machine learning.

11. The one or more non-transitory media of claim 5, wherein the operations further comprise automatically selecting, via the one or more hardware processors, two of the plurality of features from the plurality of distributions.

12. The one or more non-transitory media of claim 5, wherein the recurrent neural network includes at least one of a long short-term memory (LSTM) type of recurrent neural network or a bidirectional gated recurrent units (GRU) type recurrent neural network layer.

13. The one or more non-transitory media of claim 5, wherein the recurrent neural network includes a bi-directional neural network architecture having a plurality of nodes and configured to allow an output from a first node of the plurality of nodes to affect a subsequent input to the first node of the plurality of nodes.

14. The one or more non-transitory media of claim 5, wherein for each of the plurality of electronic health records, the comprehensive record-specific information for the defined time span comprises:

a diagnosis code and/or procedure code, that is associated with the chronic disease; and descriptions of two or more medical encounters occurring within the defined time span relative to the diagnosis code and/or procedure code associated with the chronic disease.

15. The one or more non-transitory media of claim 5, wherein the operations further comprise: embedding the first plurality of vectors for the plurality of encoded longitudinal medical histories; and prior to the presenting, processing the first plurality of vectors using the recurrent neural network.

16. The one or more non-transitory media of claim 5, wherein the operations further comprise:

embedding the first plurality of vectors for the plurality of encoded longitudinal medical histories;

embedding a second plurality of vectors for a plurality of medical concepts identified in the electronic data; and prior to the presenting:

processing the first plurality of vectors using the recurrent neural network; and processing the second plurality of vectors using the recurrent neural network.

17. The one or more non-transitory media of claim 16, wherein:

embedding the first plurality of vectors comprises:

flattening two or more features from one or more sequential observation time periods in the longitudinal medical histories, and embedding the second plurality of vectors comprises:

flattening one or more medical concepts from the longitudinal medical histories.

18. The one or more non-transitory media of claim 5, wherein the operations further comprise embedding the first plurality of vectors for the plurality of encoded longitudinal medical histories, the first plurality of vectors including one or both of diagnosis codes and procedure codes that are present in the electronic data, and producing a particular disease-agnostic onset prediction model based on the embedding.

19. The one or more non-transitory media of claim 18, wherein the operations further comprise embedding a second plurality of vectors for a plurality of medical concepts identified in the electronic data, the second plurality of vectors including information selected from a group comprising medications, allergies, care plans, provider appointments, questionnaire information, and a frequency for one or more diagnosis codes and procedure codes that are present in the electronic data, and wherein the producing of the particular disease-agnostic onset prediction model is based on the embedding of the second plurality of vectors.

20. The one or more non-transitory media of claim 5, wherein a first vector of the first plurality of vectors includes:

a gender, an age, and a race that are present in the electronic data and that are specific to a first longitudinal medical history of the plurality of encoded longitudinal medical histories; and a frequency of one or both of diagnosis codes and procedure codes that are (a) present in the electronic data and (b) specific to the first longitudinal medical history.

21. The one or more non-transitory media of claim 5, wherein the two or more of the plurality of features are selected, as corresponding to the chronic disease, based on a heat map analysis performed automatically via the one or more hardware processors.

22. A medical-information computing system having one or more hardware processors configured to perform a plurality of operations, the operations comprising:

accessing electronic data that includes a plurality of encoded longitudinal medical histories, the plurality of encoded longitudinal medical histories being created from clinical data extracted from a corresponding plurality of electronic health records, and each record of the plurality of electronic health records including (a) a defined time span associated with the record and (b) comprehensive record-specific information for the defined time span associated with the record;

receiving, via the one or more hardware processors, an indication for a chronic disease associated with at least a portion of: the defined time spans and the comprehensive record-specific information from which the plurality of encoded longitudinal medical histories are created;

in response to the receiving of the indication via the one or more hardware processors, automatically performing by the one or more hardware processors and without user input:

(a) generating a plurality of distributions for a plurality of features in the plurality of encoded longitudinal medical histories; and (b) selecting, via the one or more hardware processors and without user input, two or more of the plurality of features from the plurality of distributions, wherein the one or more hardware processors are associated with an electronic memory of a the medical-information computing system, and wherein the two or more of the plurality of features are selected as corresponding to the chronic disease;

generating an onset time period for the chronic disease, the onset time period for the chronic disease being generated (a) for a particular longitudinal medical history of the plurality of encoded longitudinal medical histories associated with the chronic disease, (b) based on a first plurality of vectors for the plurality of encoded longitudinal medical histories, and (c) based further on a recurrent neural network, wherein: the first plurality of vectors includes the two or more of the plurality of features selected from the plurality of distributions as corresponding to the chronic disease, the recurrent neural network is configured using input data that is based on input vectors of data corresponding to instances of information selected from a group comprising longitudinal medical history data, the first plurality of vectors, and chronic disease indication data, the recurrent neural network is further configured based on aligning sequential observation time periods of longitudinal medical histories relative to known dates of onset of the chronic disease for two or more of the plurality of encoded longitudinal medical histories, and an instance of the input data associated with the particular longitudinal medical history is input to the recurrent neural network to produce output prediction data indicating the onset time period for the chronic disease; and presenting, via an electronic interface and based on at least the output prediction data, the onset time period for the chronic disease, wherein presenting the onset 5 time period for the chronic disease includes communicating via the one or more hardware processors and via the electronic interface a date or a range of dates associated with the onset time period for the chronic disease. 10

* * * * *